(12) United States Patent
Ruzzo

(10) Patent No.: US 6,339,331 B1
(45) Date of Patent: Jan. 15, 2002

(54) METHODS AND APPARATUS FOR INSPECTING TV-SHAPED OPENINGS, USING EDDY CURRENT

(75) Inventor: Patsy A. Ruzzo, West Chester, OH (US)

(73) Assignee: General Electric Company, Cincinnati, OH (US)

(*) Notice: Subject to any disclaimer, the term of this patent is extended or adjusted under 35 U.S.C. 154(b) by 0 days.

(21) Appl. No.: 09/534,511

(22) Filed: Mar. 24, 2000

Related U.S. Application Data
(60) Provisional application No. 60/170,622, filed on Dec. 14, 1999.

(51) Int. Cl.[7] ............................ G01N 27/82; G01N 27/90
(52) U.S. Cl. ..................... 324/261; 324/219; 324/226; 324/262
(58) Field of Search ............................... 324/219, 220, 324/226, 234, 236–240, 261, 262; 318/578; 33/23.01, 23.08, 23.11, 545, 546, 556; 73/622, 623, 633, 634

(56) References Cited

U.S. PATENT DOCUMENTS

| | | | | |
|---|---|---|---|---|
| 3,594,626 A | * | 7/1971 | Palmer | |
| 3,714,715 A | * | 2/1973 | Coes, Jr. | |
| 3,739,262 A | * | 6/1973 | Seekins | .................. 324/262 X |
| 3,893,022 A | * | 7/1975 | Kulik et al. | ................. 324/236 |
| 3,918,299 A | * | 11/1975 | Donnadieu | .............. 324/262 X |
| 4,434,659 A | * | 3/1984 | Kurtz et al. | ............. 324/262 X |
| 4,644,274 A | * | 2/1987 | Casarcia | ..................... 324/262 |
| 5,073,332 A | * | 12/1991 | Wanhem et al. | |
| 5,339,031 A | * | 8/1994 | Chern | ........................ 324/219 |
| 5,903,147 A | | 5/1999 | Granger, Jr. et al. | |
| 6,220,099 B1 | | 4/2001 | Marti et al. | |

* cited by examiner

Primary Examiner—Gerard R. Strecker
(74) Attorney, Agent, or Firm—Andrew C. Hess; V. Ramaswamy

(57) ABSTRACT

An inspection apparatus includes a component engagement apparatus, a detection apparatus, and a movement apparatus and is controlled by a cam. A drawer is slidably attached to the component engagement apparatus to receive and align a component including a TV-shaped opening. The detection apparatus is sized to receive an eddy current probe and is attached to the movement apparatus with an adjustable fixture. The movement apparatus identifies a relative position of the eddy current probe in relation to the TV-shaped opening being inspected and guides the movement of the detection apparatus.

19 Claims, 3 Drawing Sheets

METHODS AND APPARATUS FOR INSPECTING TV-SHAPED OPENINGS, USING EDDY CURRENT

CROSS REFERENCE TO RELATED APPLICATION

This application claims the benefit of U.S. Provisional Application No. 60/170,622, filed Dec. 14, 1999.

BACKGROUND OF THE INVENTION

This invention relates generally to non-destructive inspection of components and, more particularly, to inspection of components which include TV-shaped openings.

Gas turbine engines operate under adverse conditions and are frequently inspected. Many components are manufactured with integral TV-shaped openings which induce additional stresses on the components. Therefore, the components that include the openings are frequently inspected.

Fluorescent penetrant inspection (FPI) systems typically only detect cracks that are open to the surface of the component being inspected. However, in most components which include TV-shaped openings, the components are manufactured such that any pre-manufactured openings are in compression across the component. Because the component surfaces are in compression, any stresses induced within the components are directed from the surface inward, and therefore, the cracks may not be open to the surface. Therefore the FPI systems are ineffective for use with the TV-shaped openings.

Eddy current inspection methods detect cracks that are not open to the surface by inducing eddy currents within the material under inspection. Known eddy current methods for inspecting TV-shaped openings use eddy current machines which are expensive and bulky. In addition, the eddy current machines are large, impracticable to move, and often require a large area to operate. The gas turbine engine components must be brought to the location of the eddy current machine for inspection.

BRIEF SUMMARY OF THE INVENTION

In an exemplary embodiment, an inspection apparatus includes a component engagement apparatus, a detection apparatus, and a movement apparatus. A drawer is slidably attached to the component engagement apparatus and receives and aligns a component including a TV-shaped opening into position for an inspection. The detection apparatus is sized to receive an eddy current probe and is attached to the movement apparatus with an adjustable fixture. The movement apparatus includes an indicator which identifies a position of the eddy current probe in relation to the TV-shaped opening being inspected, a cam assembly which guides movement of the movement apparatus, and a roller bearing assembly which facilitates movement of the movement apparatus.

In operation, the movement apparatus follows a cam profile which controls movement of the detection apparatus. The eddy current probe scans a portion of the TV-shaped opening and transmits data to an eddy scope. The inspection scans are then reliably repeated circumferentially around the TV-shaped opening. The inspection apparatus is easily transported from one location to another. As a result, the inspection apparatus eliminates more costly and more complicated known inspection equipment and provides a system that is accurate, portable, and cost-effective.

DETAILED DESCRIPTION OF THE INVENTION

Figure 1:
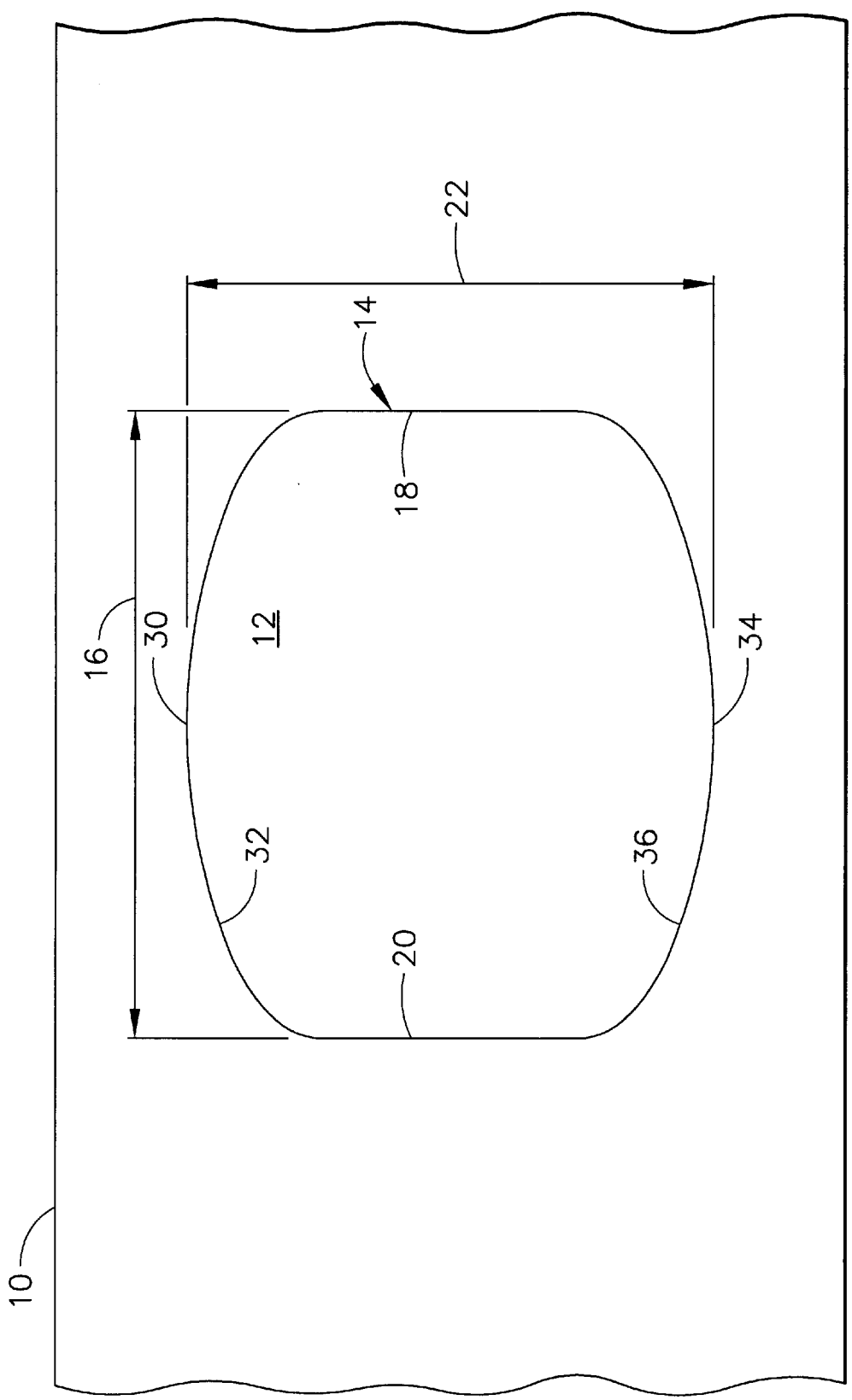
FIG. 1 is a partial plan view of a component including a TV-shaped opening.

FIG. 1 is a partial plan view of a component 10 which includes a TV-shaped opening 12. In one embodiment, component 10 is a turbine engine component which includes TV-shaped opening 12 to permit visual inspections of other components and access to other components, fasteners, and other access openings.

Opening 12 is defined by an edge 14 which is generally smooth around opening 12. Opening 12 includes a width 16 across a first side 18 and a second side 20 and a length 22 between an apex 30 of a curved third side 32 and an apex 34 of a curved fourth side 36. In one embodiment, width 16 is approximately 0.75 inches and length 22 is approximately 0.625 inches.

Figure 2:
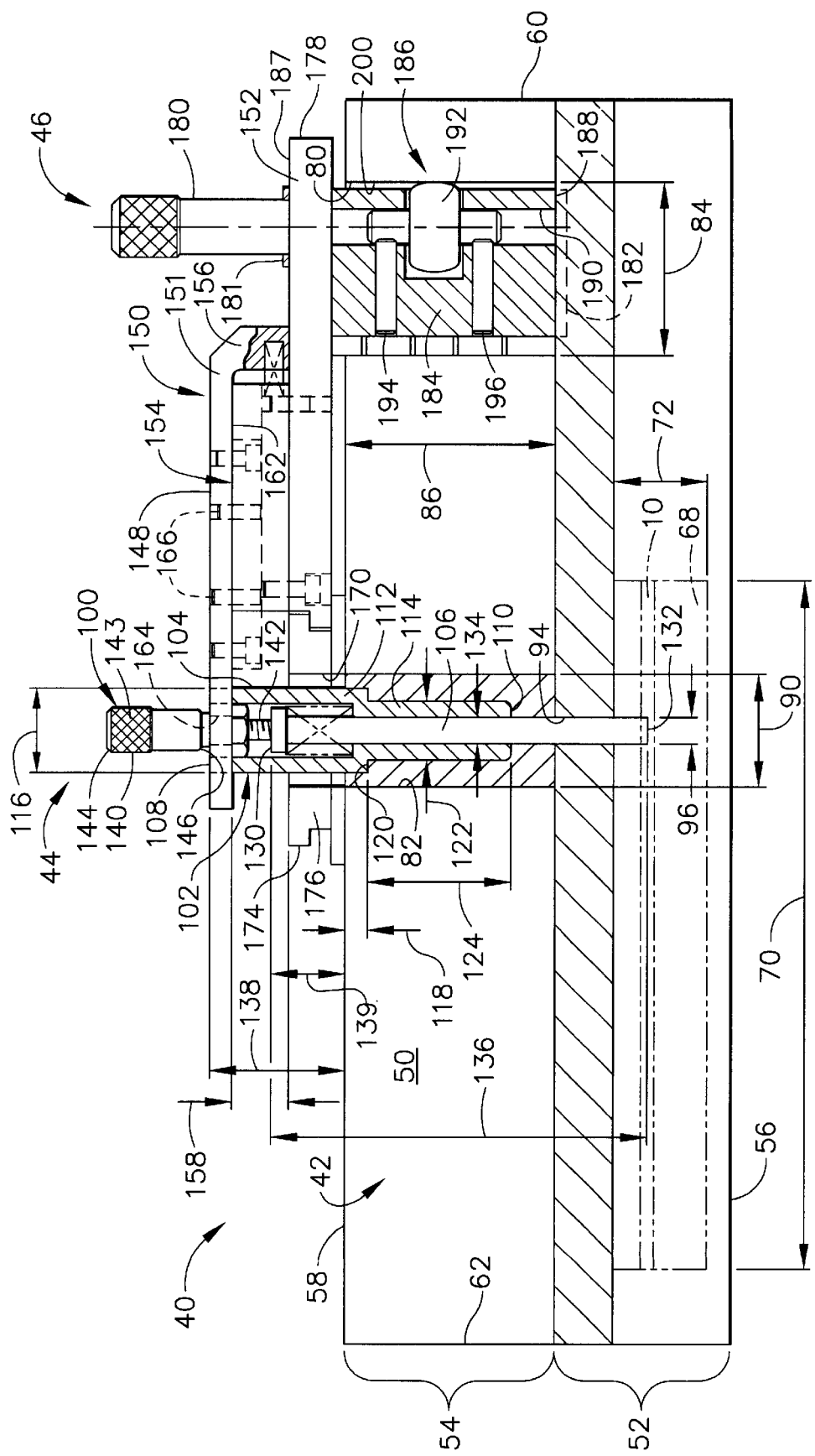
FIG. 2 is a schematic side view of a detection apparatus used to inspect components which include TV-shaped openings.

FIG. 2 is a schematic side view of an inspection apparatus 40 for non-destructive inspections of components 10 (shown in FIG. 1) which include integral TV-shaped openings 12 (shown in FIG. 1). Inspection apparatus 40 includes a component engagement apparatus 42 which receives components 10, a detection apparatus 44 which receives an eddy current probe (not shown), and a movement apparatus 46 which positions detection apparatus 44. Additionally, inspection apparatus 40 is electrically connected to an eddy scope (not shown) which electrically illustrates indications on a crt screen (not shown). Movement of the eddy current probe is controlled by movement of movement apparatus 46.

Component engagement apparatus 42 includes a body 50 which has a base portion 52 and a top portion 54 attached to base portion 52. Body 50 is generally rectangular in shape and has a substantially flat bottom surface 56 and a substantially flat top surface 58. Base portion 52 includes a first side 60 and a second side 62. A drawer 68 is slidably attached to base portion 52. Drawer 68 has a width 70 and a height 72 and is sized to receive components 10 which include TV-shaped openings 12.

Top portion 54 includes a first opening 80 and a second opening 82. First opening 80 is between second opening 82 and body first side 60. First opening 80 has a width 84 and extends substantially perpendicularly from top surface 58 through top portion 54 to base portion 52 for a depth 86. First opening 80 is sized to receive movement apparatus 46. Second opening 82 has a width 90 and extends substantially perpendicularly from top surface 58 through top portion 54 to base portion 52 for a depth 86. Second opening 82 is sized to receive detection apparatus 44. Second opening 82 is positioned between first opening 80 and body second side 62 and is concentrically positioned within top portion 54 over an opening 94 disposed within base portion 52. Opening 94 has a width 96 and extends from top portion 54 through base portion 52 into drawer 68 to provide detection apparatus 44 access to components 10 to be inspected.

Components 10 to be inspected are placed in drawer 68 such that a particular TV-shaped opening 12 to be inspected is in close proximity to opening 94. Drawer 68 includes an alignment apparatus (not shown) which positions component 10 such that the particular TV-shaped opening 12 being inspected is properly aligned with respect to opening 94, detection apparatus 44, and the eddy current probe.

Detection apparatus 44 includes an adjuster mechanism 100 and an eddy current probe holder 102. Eddy current probe holder 102 includes an outer sleeve 104 and an inner sleeve 106. Outer sleeve 104 has a first end 108, a second end 110, a first body portion 112, and a second body portion 114. First body portion 112 has a first diameter 116 which extends from first end 108 into component body top portion 54 for a distance 118 to an outer shoulder 120. Second body portion 114 has a second diameter 122 which extends from shoulder 120 to outer sleeve second end 110 for a distance 124. Second body portion 114 is concentrically aligned with first body portion 112 and second diameter 122 is smaller than first diameter 116 Inner sleeve 106 has a first end 130, a second end 132, and a diameter 134 which remains constant from first end 130 to second end 132 for a distance 136. Inner sleeve 106 is concentrically positioned within outer sleeve 104 and is sized to receive the eddy current probe.

When detection apparatus 44 is positioned within component engagement apparatus 42, outer sleeve first body portion 112 extends outward from top portion second opening 82 a distance 138 above component engagement apparatus top surface 58. Additionally, inner sleeve 106 is positioned such that inner sleeve first end 130 extends from top portion second opening 82 a distance 139 while inner sleeve second end 132 extends into component engagement apparatus drawer 68.

Inner sleeve first end 130 is rotatably coupled to adjuster mechanism 100 which adjusts a height of the eddy current probe above the particular TV-shaped opening 12 being inspected. Adjuster mechanism 100 includes a knob 140 and mechanical linkage 142 which connects knob 140 to inner sleeve 106. Rotating knob 140 clockwise lowers the eddy current probe closer to component 10 within drawer 58, and rotating knob 140 counter-clockwise raises the eddy current probe to a position above drawer 58 and the TV-shaped opening 12 being inspected. In one embodiment, adjuster mechanism knob 140 is calibrated to rotate substantially similarly to a rotation of a micrometer (not shown). Knob 140 has a knurled grip 143 adjacent a first end 144 of knob 140 which provides an easier surface for a user to grasp during rotation. A second end 146 of knob 140 is adjacent a top surface 148 of a fixture 150.

Fixture 150 extends between detection apparatus 44 and movement apparatus 46 and includes an upper arm 151, a lower arm 152, and a biasing mechanism 154. Upper arm 151 extends from a shoulder 156 attached to lower arm 152 and is substantially parallel to lower arm 152 and is separated from lower arm 152 by a distance 158. Arms 151 and 152 are substantially parallel to component engagement apparatus top surface 58.

Upper arm 151 includes top surface 148, a lower surface 162 which is substantially parallel to top surface 148, and an opening 164 which permits detection apparatus knob 140 to connect to linkage 142. Lower surface 162 is attached to biasing mechanism 154 which extends between upper arm 151 and lower arm 152. Biasing mechanism 154 includes a plurality of adjustable springs 166 which permit a user to adjust an amount of tension induced on detection apparatus 44 and thus control the amount of tension between the eddy current probe and the particular TV-shaped opening 12 being inspected.

Lower arm 152 includes an opening 170. Detection apparatus 44 extends through opening 170 and lower arm 152 extends from detection apparatus 44 to movement apparatus 46. A first end 174 of lower arm 152 includes a spacer 176 mounted circumferentially around detection apparatus 44 adjacent opening 170. A second end 178 of lower arm 152 is located adjacent movement apparatus 46.

Movement apparatus 46 includes a handle 180, an indicator 181, a cam 182, a body 184, and a roller bearing assembly 186. Handle 180 is positioned above a top surface 187 of lower arm 152 and indicator 181 is circumferentially mounted around handle 180 and is attached to top surface 187. Body 184 is attached to lower arm 152 and is positioned within component engagement apparatus first opening 80 such that a bottom surface 188 of body 184 is in slidable contact with component engagement apparatus base portion 52. Body 184 includes an opening 190 which is concentrically positioned beneath handle 180. Opening 190 is sized to receive roller bearing assembly 186 which includes a roller bearing 192 and a pair of roller bearing supports 194 and 196. During operation, roller bearing 192 is in rolling contact with a wall 200 which defines component engagement apparatus first opening 80.

Cam 182 is a TV-shaped template (not shown) which is larger than TV-shaped openings 12 included in components 10. Cam 182 is sized to receive a portion (not shown) of movement apparatus body 184 inserted within cam 182. Handle 180 is rotatably attached to body 184 and is positioned adjacent indicator 181.

During operation detection apparatus 44 is electrically connected to an eddy current machine (not shown). Knob 140 is moved manually to control movement of detection apparatus 44. Initially, an eddy current probe is inserted within detection apparatus inner sleeve 106 and component 10 is inserted within drawer 68 such that a particular TV-shaped opening is in close proximity to component engagement apparatus opening 94. After drawer 68 is closed, the drawer alignment apparatus automatically aligns component TV-shaped opening 12 with respect to the eddy current probe and opening 94. Knob 140 is rotated to adjust the height of the eddy current probe with respect to component 10. A distance of separation between the eddy current probe and the particular TV-shaped opening 12 being inspected is controlled by biasing mechanism 154.

As TV-shaped opening 12 is inspected, knob 140 is moved manually to control movement of detection apparatus 44, causing detection apparatus 44 to move. More specifically, cam 182 guides the movement of movement apparatus body 184 around the TV-shaped template of cam 182. As body 184 moves, fixture 150 simultaneously moves detection apparatus 44 such that the eddy current probe moves along edge 14 (shown in FIG. 1). The eddy current probe performs an inspection scan every degree circumferentially around edge 14 of TV-shaped opening 12 being inspected. As the eddy current probe is inspecting along edge 14 and body 184 is moving, handle 180 simultaneously rotates adjacent indicator 181 to designate a relative location of the eddy current probe with respect to TV-shaped opening 12. Accordingly, when the eddy scope indicates that the eddy current probe has located a potential flaw, indicator 181 permits a user to identify the location of the flaw within TV-shaped opening 12. Component 10 may include more than one TV-shaped opening 12. To inspect any remaining TV-shaped openings 12, drawer 68 is opened, component 10 is re-positioned, and the process is repeated.

Figure 3:
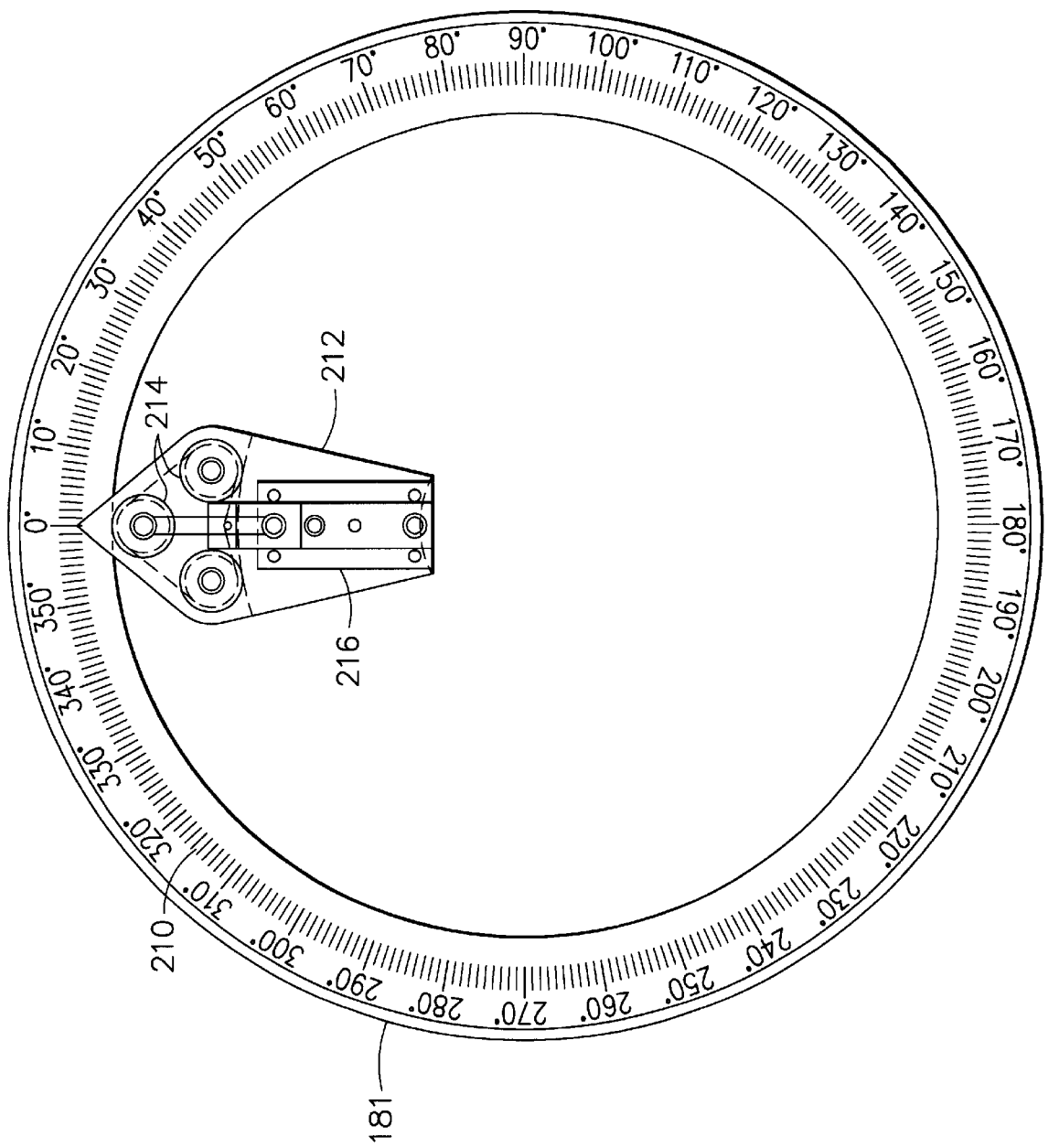
FIG. 3 is an enlarged plan view of an indicator used on the detection apparatus shown in FIG. 2.

FIG. 3 is an enlarged plan view of indicator 181 which permits a user to identify a relative location of a flaw within a TV-shaped opening 12 (shown in FIG. 1) being inspected. Indicator 181 includes an annular ring 210 and a pointer 212. Pointer 212 includes a plurality of rollers 214 which engage top surface 187 (shown in FIG. 2) of lower arm 152 (shown in FIG. 2), and a mechanical linkage assembly 216 which is connected to handle 180 (shown in FIG. 2) and movement apparatus 46 (shown in FIG. 2). Annular ring 210 is circumferentially marked in degrees. As movement apparatus 46 is guided around cam 182 (shown in FIG. 2), pointer 212 indicates the relative position of the eddy current probe with respect to TV-shaped opening 12.

The above-described inspection apparatus for inspecting TV-shaped openings is cost-effective and accurate. The apparatus includes a component engagement apparatus which automatically and reliably positions the TV-shaped opening being inspected. Additionally, the apparatus includes a movement apparatus which accurately guides an inspection apparatus circumferentially around the TV-shaped opening being inspected. Furthermore, the apparatus is portable and inexpensive when compared to known eddy current inspection apparatuses used to inspect TV-shaped openings. Accordingly, a cost-effective and accurate inspection apparatus is provided to inspect TV-shaped openings.

While the invention has been described in terms of various specific embodiments, those skilled in the art will recognize that the invention can be practiced with modification within the spirit and scope of the claims.

What is claimed is:

1. A method for inspecting components which include edges defining openings with an eddy current apparatus, the eddy current apparatus including a component engagement apparatus, a detection apparatus, and a movement apparatus, the component engagement apparatus including a body and at least one drawer slidably connected to the body, the detection apparatus configured to receive an eddy current probe, the movement apparatus attached to the detection apparatus and configured to inspect the component, said method comprising the steps of:

positioning the component to be inspected within the component engagement apparatus drawer with the detection apparatus;

positioning the eddy current probe with respect to the component with the detection apparatus; and moving the eddy current probe to inspect the edges defining the opening.

2. A method in accordance with claim 1 wherein the movement apparatus is attached to the detection apparatus with an arm, the arm including a biasing mechanism, said step of positioning the eddy current probe further comprising the step of controlling an amount of separation between the detection apparatus and the component with the biasing mechanism of the arm.

3. A method in accordance with claim 2 wherein the opening includes a TV-shaped opening, the eddy current apparatus further includes a handle rotatably attached to the movement apparatus, an indicator configured to identify a location of the movement apparatus with respect to the TV-shaped opening being inspected, a TV-shaped cam configured to guide the movement apparatus, said step of moving the eddy current probe further comprising the step of guiding movement of the movement apparatus with the cam guide such that the indicator identifies the location of the movement apparatus with respect to the TV-shaped opening being inspected.

4. A method in accordance with claim 3 wherein the eddy current apparatus further includes an adjuster and an eddy current probe holder, the adjuster rotatably coupled to the detection apparatus and configured to adjust a height of the eddy current probe with respect to the TV-shaped opening being inspected, said step of positioning the eddy current probe further comprising the step of rotating the adjuster to position the height of the eddy current probe with respect to the TV-shaped opening being inspected.

5. A method in accordance with claim 4 further comprising the step of using the component engagement apparatus drawer to align the TV-shaped openings with respect to the detection apparatus.

6. Apparatus for inspecting components that include edges which define openings, said apparatus comprising:

a component engagement apparatus configured to receive the component being inspected, said component engagement apparatus comprising a body and at least one drawer slidably connected to said body and sized to receive the component therein;

a detection apparatus configured to receive an eddy current probe for inspecting the component received within said component engagement apparatus drawer; and a movement apparatus attached to said detection apparatus and configured to position said detection apparatus with respect to said component engagement apparatus.

7. Apparatus in accordance with claim 6 further comprising an arm comprising a biasing mechanism, said movement apparatus attached to said detection apparatus with said arm, said biasing mechanism configured to adjust an amount of tension induced on said detection apparatus.

8. Apparatus in accordance with claim 7 wherein the openings include TV-shaped openings, said movement apparatus comprises a rotatable handle, an indicator configured to identify a location of said movement apparatus with respect to the TV-shaped opening being inspected, and a cam configured to guide said movement apparatus.

9. Apparatus in accordance with claim 8 wherein said movement apparatus further comprises a plurality of roller bearings and roller bearing supports.

10. Apparatus in accordance with claim 8 wherein said detection apparatus comprises a rotatable adjuster coupled to said detection apparatus and configured to adjust a height of an eddy current probe with respect to the TV-shaped opening being inspected.

11. Apparatus in accordance with claim 10 wherein said cam is TV-shaped and guides said movement apparatus circumferentially around the component TV-shaped opening.

12. Apparatus in accordance with claim 11 wherein said apparatus drawer configured to receive and align the components with respect to the detection apparatus.

13. Apparatus in accordance with claim 6 wherein said drawer configured to receive the components.

14. Apparatus in accordance with claim 12 wherein said drawer configured to align the component TV-shaped openings with respect to the detection apparatus.

15. An inspection apparatus for use with an eddy current probe to inspect a component which includes at least one opening, the apparatus comprising:

a holder assembly configured to receive the eddy current probe; and a guide assembly attached to said holder assembly and configured to position the holder assembly with respect to the opening, said guide assembly comprising a cam configured to position said holder assembly with respect to the component, wherein the component is positioned within an enclosure that is slidably coupled to the inspection apparatus.

16. An apparatus in accordance with claim 15 further comprising a body and a drawer slidably attached to said body, said drawer configured to receive the component.

17. An apparatus in accordance with claim 16 further comprising a fixture extending between said holder assembly and said guide assembly, said fixture adjustable to control an amount of tension induced on said holder assembly by said guide assembly.

18. An apparatus in accordance with claim 17 wherein the opening is a TV-shaped opening and said cam is a TV-shaped cam, said holder assembly comprises an adjuster configured to position a height of an eddy current probe with respect to the TV-shaped opening being inspected.

19. An apparatus in accordance with claim 16 wherein the components are gas turbine engine components, said drawer configured to align said opening with respect to said holder assembly.

* * * * *